US00PP34419P2

(12) United States Plant Patent
Hansen

(10) Patent No.: US PP34,419 P2
(45) Date of Patent: Jul. 12, 2022

(54) ***AMSONIA* PLANT NAMED 'STRING THEORY'**

(50) Latin Name: ***Amsonia hubrichtii* (Woodson)**
Varietal Denomination: 'String Theory'

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,866

(22) Filed: Nov. 29, 2021

(51) Int. Cl.
*A01H 5/02* (2018.01)
*A01H 6/08* (2018.01)

(52) U.S. Cl.
USPC ..... Plt./263.1
CPC ..... *A01H 6/08* (2018.05)

(58) Field of Classification Search
USPC ..... Plt./263.1
CPC ..... A01H 6/08; A01H 5/02
See application file for complete search history.

*Primary Examiner* — Keith O. Robinson

(57) ABSTRACT

A new and distinct *Amsonia* plant named 'String Theory' characterized by winter-hardy, compact, densely-stemmed, clean habit with linear, dark-green foliage that goes dormant in the winter; single, light periwinkle-blue, star-shaped flowers on medium height scapes flowering above the foliage beginning about early-May and effective for about four weeks. The new plant is useful in the landscape as a specimen or en masse and also as a cut flower.

2 Drawing Sheets

Botanical classification: *Amsonia hubrichtii* (Woodson).
Variety denomination: 'String Theory'.

STATEMENT REGARDING PRIOR DISCLOSURES UNDER 37 CFR 1.77(b)(6)

The first non-enabling disclosure of the claimed plant, in the form of a website to the public and email release to customers, was made by Walters Gardens, Inc. on Dec. 1, 2019. Since then, Walters Gardens, Inc. used photographs and descriptions of the new plant in their "Walters Gardens 21-22 Catalog" released on May 21, 2021 and sold the first plants on May 3, 2021. Walters Gardens, Inc. obtained the new plant and information about the new plant directly from the inventor. No plants of *Amsonia* 'String Theory' have been sold, in this country or anywhere in the world, nor has any disclosure of the new plant been made more than one year prior the filing date of this application, and such sale or disclosure within one year was either derived directly or indirectly from the inventor.

BACKGROUND AND ORIGIN OF THE PLANT

The present invention relates to a new and distinct Blue Star plant, *Amsonia* 'String Theory' hereinafter also referred to as the new plant or just the cultivar name, 'String Theory'. *Amsonia* 'String Theory' was hybridized by the inventor in the spring of 2014 in a trial field at a wholesale perennial nursery in Zeeland, Mich., USA. The new plant originated from a breeding program conducted by the inventor with the specific intention to improve the garden worthiness, expand color regimens and increase flowering period which were some of the criteria of further trials in the trial beds at the same nursery in Zeeland, Mich. The cross was an intentional self-pollination of a propriety unnamed selection of *Amsonia hubrichtii* known only by the breeder code 11-12 (not patented) in the spring of 2014. Seeds from the cross were collected on Sep. 16, 2014. The new plant was selected as a single seedling from this cross, and after confidential evaluations in a trial bed beginning in 2016 in Zeeland, Mich. the new plant resulting from a single seedling was assigned the breeder code 14-3-2 through the remaining trial period prior to assigning a cultivar name.

The new plant has been asexually propagated by shoot tip cuttings at the same wholesale nursery in Zeeland, Mich. since 2016 with all resultant asexually propagated plants having retained all the same unique traits as the original plant. *Amsonia* 'String Theory' has proven to be stable and reproduces true to type in successive generations of asexual reproduction.

The most similar Blue Star cultivars known to the inventor are: 'Blue Ice' (not patented), 'Starstruck' U.S. Plant Pat. No. 32,246 and 'Storm Cloud' (not patented). 'Blue Ice' is shorter and less horizontal in habit, more compact with darker blue flowers and broader foliage. 'Starstruck' is slightly shorter in habit, with broader foliage. 'Storm Cloud' is taller in habit, with darker purple in the stems, much wider foliage with more significant silver veining, and the flowers are a deeper blue. Compared with typical *Amsonia hubrictii* the new plant has a shorter, denser and more upright habit. The parent is taller with a more open broader habit.

*Amsonia* 'String Theory' differs from all other Blue Star plants known to the applicant, by the combination of the following traits:

1. Winter-hardy to USDA zone 4, compact, densely stemmed, clean, with foliage that goes dormant in the winter;
2. Pale-blue star-shaped flowers in clusters near the end of the stems;
3. Flowering above the foliage in mid-spring on dense panicles for about three to four weeks;
4. Narrow dense foliage that is dark green until early fall when it develops a golden-orangish fall color;

5. Foliage and stems have white latex sap making the plants undesirable to deer and rabbits.

BRIEF DESCRIPTION OF THE DRAWINGS

The photograph of the new plant demonstrates the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
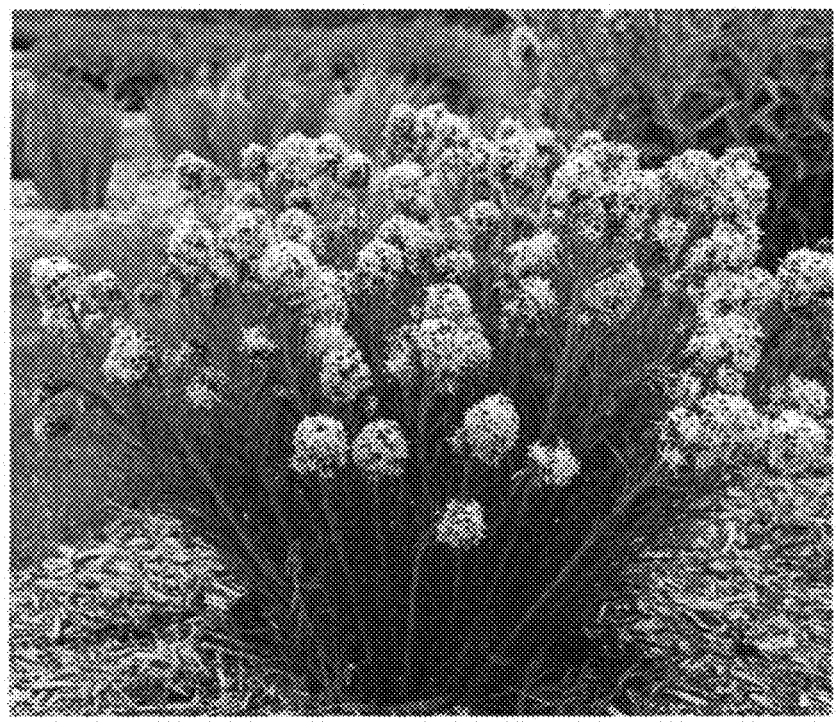
FIG. 1 shows a six-year-old plant in peak flower during mid-summer in a full-sun trial garden in Zeeland, Mich.
Figure 2:
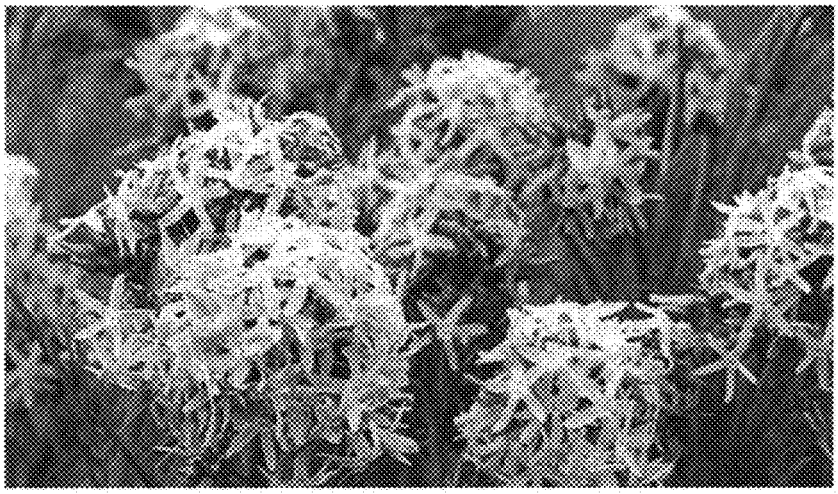
FIG. 2 shows a close-up of the flower and buds.
Figure 3:
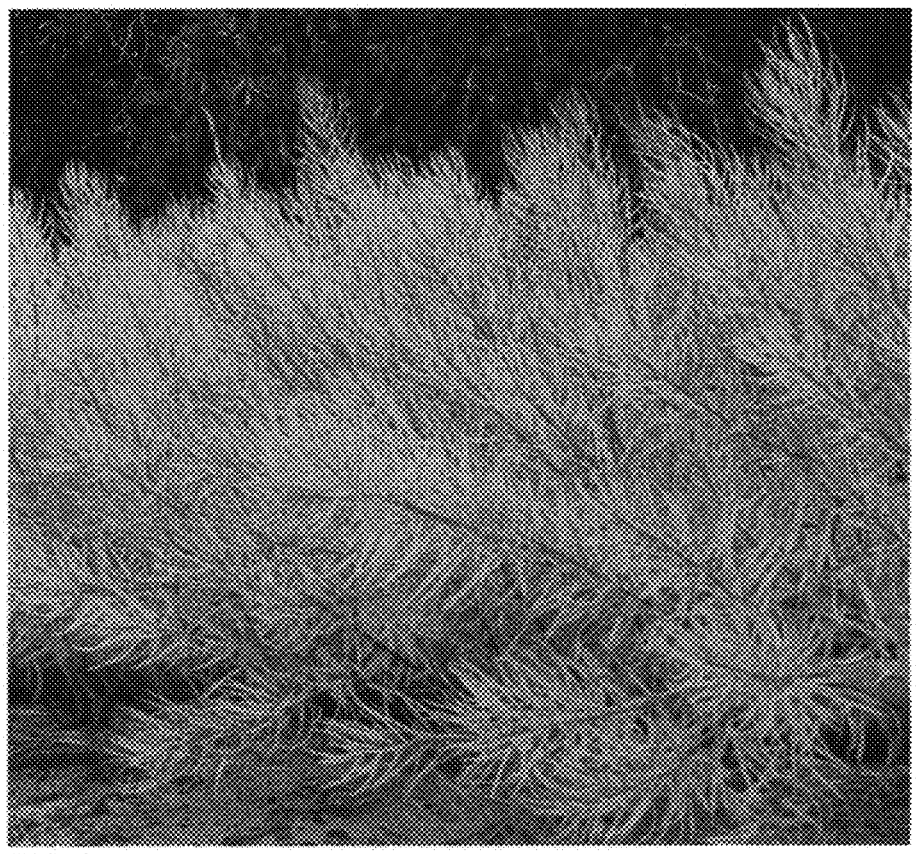
FIG. 3 shows the foliage with golden-orangish foliage fall color.

The following descriptions and color references are based on the 2015 edition of The Royal Horticultural Society Colour Chart except where common dictionary terms are used. The new plant, *Amsonia* 'String Theory', has not been observed under all possible environments. The phenotype may vary slightly with different environmental conditions, such as temperature, light, fertility, moisture and maturity levels, but without any change in the genotype. The following observations and size descriptions are of a seven-year-old plant in a sunny research garden bed in Zeeland, Mich. with and supplemental water and fertilizer.

Botanical classification: *Amsonia hubrichtii;*

Parentage: The parent is a proprietary unreleased selection of *A. hubrechii;*

Propagation: Division of the rhizome and shoot tip cuttings;

Growth rate: Initially slow, moderate with maturity;

Crop time: About 15 to 20 weeks starting in early summer to grow a 2.5 cm plug to a flowering 3.8 liter container after vernalization;

Plant shape and habit: Winter-hardy herbaceous perennial with numerous stems with dark green foliage in a dense mound;

Plant size: Foliage height about 86 cm tall and about 180 cm wide about 50 cm above the soil, from soil line to the top of the flowers about 45 cm tall;

Rooting habit: Primary roots thick, fleshy and seldom branched, to 30 cm long and 5.0 mm thick, color between RHS 165B and RHS 165C; depending on soil type; secondary roots fibrous, to about 6 cm long and 1.0 mm diameter, color between RHS 158D and RHS 165D depending on soil type;

Leaves: Linear; alternate; entire; glabrous and lustrous adaxial, glabrous and glaucous abaxial; apex narrowly acute, base attenuate; about 112 leaves per stem; to about 74.0 mm long and 4.0 mm across near middle; average about 61 mm long and 3.4 mm wide; attitude mostly outright; no fragrance observed;

Leaf color: Expanding adaxial nearest RHS 137A and abaxial nearest RHS 138A without significant anthocyanin; mature adaxial nearest RHS 137A, and abaxial between RHS 147B RHS 146B; fall color variable, nearest RHS 22B, and between RHS 23B and RHS 23C, with touches of nearest RHS N163C;

Petiole: Short; to about 3.0 mm long and 1.0 mm across; glabrous; glaucous;

Petiole color: Between RHS N144A and RHS 146D;

Veins: Pinnate; adaxial puberulent; abaxial glabrous;

Vein color: Mature and expanding adaxial midrib nearest RHS 151A and secondary adaxial veins nearest RHS 137A; mature and expanding abaxial midrib between RHS 146D and RHS 145C and secondary veins nearest RHS 147C;

Stem: Cylindrical; glabrous; glaucous; to 40 cm tall and 7.0 mm diameter at base; with about 54 nodes per stems below flowering branches; average internode length about 1.4 cm;

Branches: About 3 to 5 per stem; beginning at about 40 cm above soil and below flowers, extending above flowers; to about 39 cm long and 4.0 mm diameter;

Stem color: As emerging with leaves still tight nearest RHS 137A and RHS N187A, at flowering time nearest RHS 146C and with fall color variable between RHS 178B and RHS 178C and between RHS 199D and RHS 161C;

Inflorescence: Branched panicle densely flowered in terminal portion; flowering about 8.0 cm across and 8.5 cm tall; about 50 to 60 flowers per panicle; inflorescences remain effective beginning early-May repeating for approximately four weeks in Zeeland, Mich.;

Flowers: Rotate, salverform; single; perfect; complete; actinomorphic; upward and outwardly facing; about 14.0 mm across in face and 8.0 mm tall, corolla tube about 7.0 mm long and 2.0 mm diameter at stigma height and 1.5 mm diameter at base; corona in center eye, about 3.0 mm across and 1.0 mm tall; individually lasting for about five to seven days;

Flower fragrance: None detected;

Buds one to two days prior to opening: Oblong with rounded apex and base; about 9.0 mm long and about 2.0 mm in diameter at widest point with near middle;

Bud color one day from opening: Between RHS 97C and RHS 91C;

Petals: Five; made up of fused corolla tube and perpendicular flattened limb; limb portion lanceolate, separate, not overlapping, with acute apex; limb portion about 7.0 mm long and 1.5 mm across just above fusion; corolla tube puberulent in abaxial distal one half and glabrous in limb; also pubescent adaxial in the 2.0 mm below corona, glabrous elsewhere;

Petal color: Adaxial face between RHS 95D and RHS 97C, with 1.0 mm center eye between RHS 97D and RHS NN155C; abaxial face between RHS 97C and RHS 92D; adaxial corolla tube nearest RHS 155C and base nearest RHS NN155C; abaxial corolla tube basal 4.0 mm between RHS 97D and RHS 92C, nearest RHS 96D distally, basal 4.0 mm between RHS 92C and RHS 92D, center portion between RHS 145A and RHS 146D; corona nearest RHS 155C; hairs nearest RHS NN155D;

Pedicel: Cylindrical; glabrous; matte; average about 3.0 mm long and 0.5 mm diameter extending to about 6.0 mm long with seed development; upright and outright;

Pedicel color: Nearest RHS 146A;

Peduncle: Cylindrical; glabrous; matte; typically one per division; just below flowering portion about 3.5 mm diameter at base, average 8.0 cm tall; extending above foliage at time of flowering; branches to about 3.0 cm long and 1.5 mm diameter;

Peduncle color: Nearest RHS 146C and lightly maculate distally to nearest RHS 176C;

Gynoecium: Single, split; about 6.0 mm long;

*Style.*—Single; cylindrical; glabrous; about 3.5 mm long, 0.3 mm diameter; color nearest RHS NN155D.

*Stigma.*—Globose; about 0.5 mm across; color nearest RHS 144A.

*Ovary.*—Superior; split; globose; about 1.0 mm across and 1.2 mm long; color nearest RHS 138A.

Androecium: Five; adnate to inner corolla;

*Filaments.*—Five; adnate to inner corolla and extending about 6.0 mm to 7.0 mm above corolla base, and free in distal 1.0 mm; about 0.2 mm in diameter; color nearest RHS NN155D.

*Anthers.*—Oblong; basifixed, longitudinal; about 1.0 mm long and 0.5 mm wide; color closest to RHS N92C.

*Pollen.*—Abundant; color nearest RHS 158B.

Fruit: Slender; upright; non-fleshy; dried follicle; singled seeded in diameter; dehiscing along a longitudinal spiral; to about 11.5 cm long and 3.0 mm in diameter; color while maturing nearest RHS 138B and at dehiscence between RHS 156D and RHS 158C;

Seed: Up to about 11 per follicle; cylindrical; apices and bases either truncate or angular; asperous; to about 12.0 mm long, about 2.0 mm diameter; color variable, between RHS 166B and RHS 166A and nearest RHS 200B;

Disease and pest resistance and tolerance: 'String Theory' shows typical Blue Star resistant to deer and rabbits but has not shown resistance or susceptibility to diseases and pests beyond that common for Blue Star plants. The plant grows best and shows best coloration with full-sun, plenty of moisture, adequate drainage, but is able to tolerate some drought when mature and direct sun without leaf burn when provided sufficient water.

Hardiness at least from USDA zone 4 through 9. The new plant is useful for landscaping en masse, as a single specimen or small groups, as a container plant or as a cut flower.

I claim:

1. A new and distinct ornamental Blue Star, *Amsonia* plant named 'String Theory' as herein described and illustrated.

* * * * *